(12) United States Patent
Rastopov

(10) Patent No.: US 7,209,231 B2
(45) Date of Patent: Apr. 24, 2007

(54) OPTICAL DETECTION OF PARTICLES IN A LIQUID MEDIUM

(75) Inventor: Stanislav Rastopov, Moscow (RU)

(73) Assignee: Rusteck Ltd., St. Helier, Jersey (GB)

( * ) Notice: Subject to any disclaimer, the term of this patent is extended or adjusted under 35 U.S.C. 154(b) by 98 days.

(21) Appl. No.: 10/416,780

(22) PCT Filed: Nov. 15, 2001

(86) PCT No.: PCT/IB01/02763

§ 371 (c)(1),
(2), (4) Date: Nov. 6, 2003

(87) PCT Pub. No.: WO02/40961

PCT Pub. Date: May 23, 2002

(65) Prior Publication Data

US 2004/0070756 A1    Apr. 15, 2004

(30) Foreign Application Priority Data

Nov. 15, 2000   (GB)   ............................ 0027904.2

(51) Int. Cl.
*G01N 21/00*   (2006.01)
(52) U.S. Cl. ................................................. 356/339
(58) Field of Classification Search ............... 356/39, 356/335–343
See application file for complete search history.

(56) References Cited

U.S. PATENT DOCUMENTS

| 3,975,084 A | * | 8/1976 | Block | 356/335 |
| 4,762,413 A | | 8/1988 | Namba et al. | 356/339 |
| 5,296,910 A | * | 3/1994 | Cole | 356/28.5 |
| 5,846,759 A | | 12/1998 | Rastopov et al. | 435/29 |
| 5,993,053 A | * | 11/1999 | Clark | 366/146 |
| 6,191,853 B1 | * | 2/2001 | Yamaguchi et al. | 356/336 |
| 6,885,440 B2 | * | 4/2005 | Silcott et al. | 356/73 |

FOREIGN PATENT DOCUMENTS

| EP | 0 184 269 | 6/1985 |
| GB | 2 235 764 | 3/1991 |
| JP | 63029232 | 2/1988 |
| JP | 63095341 | 4/1988 |
| JP | 1140044 | 6/1989 |
| WO | WO 88/02855 | 4/1988 |

* cited by examiner

*Primary Examiner*—Gregory J. Toatley, Jr.
*Assistant Examiner*—Isiaka O. Akanbi
(74) *Attorney, Agent, or Firm*—Westman, Champlin & Kelly, P.A.

(57) ABSTRACT

Particles in a liquid medium are detected by directing a source of laser light through a container containing a liquid sample with a concentration of microscopic particles in suspension. An optical detector located off the optical axis receives scattered light from the particles and provides a signal with a dc component and a varying component. The DC component is removed to provide a filtered signal representing the varying component. Movement is produced in the sample liquid, e.g., by convective stirring, to extend the band of frequencies of the varying component towards higher frequencies. The apparatus can be used for growth curve detection of biological samples and provides increased sensitivity.

16 Claims, 5 Drawing Sheets

OPTICAL DETECTION OF PARTICLES IN A LIQUID MEDIUM

CROSS-REFERENCE TO RELATED APPLICATION

This Application is a Section 371 National Stage Application of International Application No. PCT/IB01/02763, filed Nov. 15, 2001 and published as WO 02/40961 on May 23, 2002, not in English.

FIELD OF THE INVENTION

The present invention relates to optical apparatus for detecting particles in a liquid medium and is particularly concerned with the detection of bacteria and a method of growth curve analysis of liquid biological samples using optical techniques.

BACKGROUND OF THE INVENTION

Optical techniques have been used for some years for the detection and classification of particles in liquids. The concentration of particles in a liquid can be measured using a turbidimeter. A beam of light is transmitted through a liquid sample and attenuation of the light received at a detector provides a measure of the concentration of particles in the sample. Reference is made to Blackburn C de W, et al, (1987) "Brief Evaluation of a Fully Automated Optical Analyser System, the Bioscreen for Measuring the Growth of Micro-organism". Technical Notes No. 57, Leatherhead Food R. A.

It is also known to monitor light scattered from particles in a liquid sample. The total amount of light scattered from an illuminated volume of sample and received at a detector can provide an indication of the concentration of scattering centres or particles in the sample. This technique is called nephelometry and has been used for immunoassay reaction detection.

Techniques have also been described using coherent light from a laser and monitoring the speckle pattern produced in the light scattered from particles in the sample. Both the effect of interference between light from different scattering centres in the sample due to different path lengths to the detector, and the effect of small Doppler changes in wavelengths of scattered light due to particle motion, have been investigated. U.S. Pat. No. 4,826,319 and U.S. Pat. No. 6,011,621 describe measuring or monitoring the size of particles in a liquid by observing the frequency content of the scattered light.

It has also been proposed to detect living micro-organisms in liquid samples by observing the characteristic frequencies of intensity fluctuations of scattered light-resulting from the motility of the organisms. See, for example, "Spectral Analysis of Laser Light Scattered from Motile Micro-organisms", by R. Nossal, Biophysical Journal Vol. 11 (1971), pp341–354. However, there are substantial technical problems in using such techniques for practical purposes, especially for samples with low concentrations of micro-organisms or other particulates.

For the theory and a mathematical analysis of coherent light scattering from particles suspended in a liquid, reference should be made to "Photon Correlation and Light Beating Spectroscopy" edited by H. Z. Cummins and E. R. Pike, Plenum Press, 1974, especially pages ?–?.

SUMMARY OF THE INVENTION

The present invention provides optical apparatus for detecting particles in a liquid medium, comprising a container for a liquid sample with a concentration of microscopic particles in suspension, a source of coherent light arranged to direct coherent light along a predetermined optical axis through a sample in said container to provide an illuminated volume of said sample, a detector located off said optical axis and arranged to receive light from said source which has been scattered by particles in said illuminated volume of said sample, said detector providing a signal representing the intensity of said received light and comprising a dc component dependent on the concentration of said particles in said illuminated volume and a time varying component with frequencies in a band, a filter removing said dc component to provide a filtered output signal, and a sample stirring device to produce movement of the sample liquid in said illuminated volume so as to extend said band of frequencies towards higher frequencies.

The total intensity of light received by a detector from an illuminated volume of liquid sample is dependent on, amongst other things, the number of scattering particles in the volume. However, this total intensity also contains the following additional components:
a) a component dependent on molecular scattering by the molecules of the liquid of the sample,
b) components dependent upon absorption of light by the liquid and the material of the sample container,
c) a component dependent on scattering by the material of the sample container, and
d) a component dependent on scattering and absorption in the window of the photo detector device.

Accordingly, the component which is representative of the amount of light being scattered from particulates (in particular from bacteria or other micro-organisms) in the sample can be only a relatively small proportion of the total received signal, especially for low particle concentrations.

The present invention removes the dc component of the total scattered intensity signal from the detector, to provide a filtered signal representing only the variations in the total intensity. By using a coherent light source, such as a laser, to provide the illuminated volume of the sample, the amplitude of the variations of the scattered light intensity is also representative of the number of scattering particles within the sample volume. Interference between light scattered from individual particles within the illuminated volume produces an interference pattern (speckle pattern) at the plane of the detector. Because the scattering particles within the illuminated volume of the liquid sample are in motion, experiencing Brownian motion at least, the speckle pattern is continuously changing, producing the variations in the intensity signal from the detector. The amplitude of these intensity variations is generally proportional to the number of scattering centres or particles in the illuminated volume.

Importantly, the other sources of scattered light received by the detector tend not to produce variations in the detected intensity. As a result, filtering out the dc component of the detected intensity, produces a signal which can represent the concentration of scattering particles within the illuminated volume with much greater sensitivity.

According to theory, as set out in Cummins and Pike referenced above, it can be shown that the spectral content of variations in the intensity of scattered light from particles moving solely with Brownian motion, include substantial power density at very low frequencies (of intensity variation), down to 0.1 Hz and less for particles of 1µ size and low scattering angles (e.g. 5–7 deg). By comparison, the energy at higher variation frequencies, say 10 Hz or more, is 1000 times less. By stirring the sample liquid to produce movement of the liquid in the illuminated volume, the detected intensity variations are pushed towards higher frequencies, and it becomes possible to filter out the dc component of the detected intensity of scattered light effectively without using a filter with an excessively long time constant.

As a result, the optical apparatus described above can detect changes in the concentration of scattering particles in a sample fluid with great sensitivity and with a shorter response time. Importantly, where the optical apparatus is used for monitoring the growth curve of biological samples containing a growth medium, growth of the biological species in the particular medium can be detected much sooner and at much lower concentrations.

Conveniently, the sample stirring device comprises a heater arranged to heat the sample in the container to produced convective stirring. In order to achieve the required extension of the bandwidth of the frequency of intensity variation, the stirring device should produce a velocity of liquid movement of the order of one millimeter per second. Preferably, the stirring action of the stirring device provides liquid motion in different directions in different parts of the illuminated volume of the sample. As a result, the stirring action itself produces corresponding changes in the speckle pattern formed in the plane of the detector. It has been found that the half band or relaxation frequency of the frequency spectrum of intensity variation of the scattered light is substantially linearly related to the mean speed of motion of liquid in the illuminated volume of the sample caused by the stirring device. A relatively low level of stirring action in the liquid sample can increase the half band frequency from as low as 0.1 Hz for Brownian motion of 1 µparticles in still liquid, to 200 to 300 Hz or more. As a result, the filter can be set with a lower cut off frequency of about 10 Hz and still pass a substantial proportion of the energy contained in the spectrum of intensity variation for the scattered light.

As mentioned above, sufficient stirring of the liquid sample can be achieved using a heater. Preferably, the heater comprises a heater block for receiving said container, the heater block being asymmetric about a vertical plane containing the optical axis. In this way, the heater can be arranged to heat the sample differentially in a horizontal plane to ensure adequate convective stirring of the sample to produce the required bandwidth extension to higher frequencies.

In a preferred embodiment, the apparatus comprises at least a first matched pair of said detectors equally spaced at a common radial distance on opposite sides of a plane containing said optical axis, and difference means receiving input signals respectively from said pair of detectors and providing a different signal representing the difference between said input signals. In this way, correlated signal variations received by both detectors symmetrically spaced on opposite sides of the plane containing the optical axis are rejected in the difference signal. On the other hand, the intensity variations received by each detector which are dependent on interference in the scattered light, are not correlated and so the amplitude of the non correlated signal variations will be additive in the difference signal to produce a total amplitude equal to $\sqrt{2}$ times the amplitude of variation from each of the two detectors. In this way, the signal to noise ratio for the desired intensity variation signal can be substantially increased. Common mode signal variations which would be characteristic of many noise sources in the apparatus, are received equally and in phase by the two matched detectors of the pair and cancel each other in the difference signal. In particular, all intensity variations resulting from noise in the light source should be cancelled in this way.

The apparatus may include one or more further said pairs of detectors. A respective difference signal is obtained from the outputs of the detectors of each pair and the various difference signals can then be summed so as further to increase the sensitivity for detection of variations in the scattered light resulting from changes in the interference pattern caused by motion of the scattering particles in the illuminated volume of sample liquid.

Very preferably, the or each detector has a sensitive aperture which is greater than ten times the coherence area for interfering scattered light at the detection plane normal to the optical axis. The coherence area is a measure of the grain size of the speckle pattern at the plane of the detector caused by interference between light scattered by the various particles in the illuminated volume of the sample. Classical theory for the detection of intensity variations resulting from the speckle pattern suggests that the aperture at the detector should normally be in the range of 1 to 5 coherence areas (see "Biochemical Applications of Laser Rayleigh Scattering" by N. C. Ford, Jr., Chemica Scripta 1972, 2, 193–206). However, it has been found that better signal to noise is obtained using a relatively large illuminated volume of sample (which would lead to a small coherence area at the detector), in combination with a relatively large aperture of detector embracing a substantial number of coherence areas. The overall dc level of signal produced by the detector is then increased in proportion to the increase in area, and it has been found that the amplitude of variations in the output signal are also increased in proportion to the square root of the increase in area.

In practice, the illuminated volume of said sample may have an area normal to the optical axis which is greater than 1 $mm^2$.

Also, the illuminated volume may have a dimension along the optical axis which is greater than 3 mm, and preferably greater than 7 mm. Overall, the illuminated volume may be greater than 3 $mm^3$, and preferably greater than 30 $mm^3$.

The sensitive detector aperture may be between 0.5 and 2 $mm^2$.

The distance between the mid point of the illuminated volume along the optical axis and the detection plane may be between 1 and 10 cm.

The present invention also provides a method of growth curve analysis of a liquid biological sample comprising the steps of:

preparing a liquid sample for analysis containing a selected growth medium, illuminating a volume of said sample with coherent light directed along an optical axis, detecting the intensity of light scattered from said illuminated volume, filtering out a dc component of said detected intensity to provide a filtered signal representing only intensity variations in a predetermined band of frequencies, monitoring said filtered signals over a period of time, and determining from changes in said filtered signal the likely presence or absence of a biological species which is viable in the selected growth medium.

By monitoring only the intensity variations in light reflected from an illuminated sample, changes in the concentration of scattering centres in the sample, which will normally represent a change in the population of a biological species in the sample, can be detected with much greater sensitivity and therefore at a much earlier stage in the development of a growth path.

Preferably, the method includes the step of producing motion of the liquid of said sample relative to the optical axis. As explained above, this shifts the frequencies of the intensity variations to higher frequencies, allowing a greater total energy of the intensity variation signal to be detected whilst eliminating the dc content, without using filters with excessive time constants.

Preferably the band of frequencies monitored is from 1 Hz to 500 Hz, and more preferably between 10 Hz and 300 Hz.

BRIEF DESCRIPTION OF THE DRAWINGS

Examples of the present invention will row be described with reference to the accompanying drawings, in which.

DETAILED DESCRIPTION OF THE PREFERRED EMBODIMENTS

Figure 1:
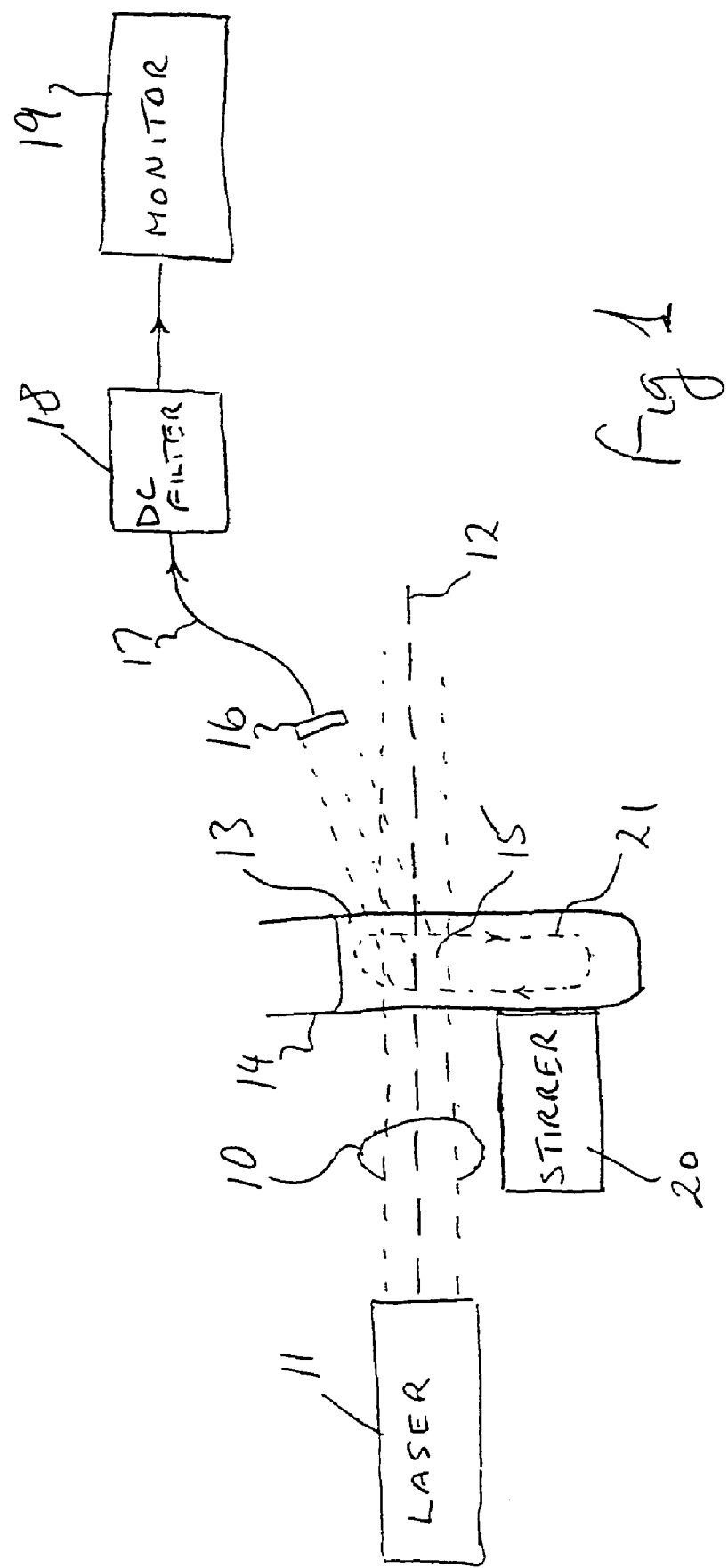
FIG. 1 is a schematic illustration of particle detection apparatus embodying the present invention.

Referring to FIG. 1, a beam 10 from a laser 11 is directed along an optical axis 12 through a liquid sample 13 contained in a sample holder or cuvette 14. The cuvette 14 is made from a material which is substantially transparent to the laser light, or at least has a transparent window through which the laser beam can enter the cuvette to illuminate the liquid sample 13, and a further transparent window through which light scattered from particles in an illuminated volume 15 of the liquid can pass to a detector 16.

As illustrated, the laser beam 10 is substantially collimated so that the illuminated region 15 of sample liquid within the cuvette 14 has a volume corresponding to the product of the cross-sectional area of the laser beam and the width of the cuvette in the direction of the optical axis 12. Also, in the illustrated example, scattered light from all parts of the illuminated region 15 of the liquid sample can reach the sensitive area of the photodetector 16.

The photodetector 16 produces on line 17 a signal representing at any time the intensity of scattered light received by the detector. This signal on line 17 is filtered in a dc filter 18 to remove the dc component of the signal so that only the variations in the received signal are passed to a monitor 19.

It is important to note that, by comparison with prior art photometric apparatus such as disclosed in U.S. Pat. Nos. 4,826,319 and 6,011,621, the apparatus described in this embodiment of the invention is not concerned with detecting or analysing the spectral content of variations in light scattered from the liquid sample. In this example of the invention, it is the total energy in these signal variations which is being detected and monitored.

Furthermore, it should be understood that the described embodiment is particularly concerned with the analysis of liquid samples with relatively low concentrations of scattering particles.

As mentioned before, the amplitude of variations in the scattered signal detected by the detector 16 has a generally proportional relationship to the concentration of scattering centres. However, in practice, the detector 16 must have a dynamic range sufficient to accommodate the dc level of scattered light from the large illuminated volume 15, and still sufficiently low noise to permit the much smaller fluctuation amplitude still to be detected.

The described apparatus may be compared with nephelometry in which the intensity of scattered light is monitored, but instead the described apparatus uses a coherent light source and filters out the dc level of the scattered light intensity signal so as to use the fluctuation amplitude as the measuring parameter for particle concentration in the sample.

The laser 11 may be a solid state semiconductor laser operating at 670 nm. The wavelength is not however critical for many applications. The laser 11 produces a collimated beam having a cross-sectional area greater than about 1 mm$^2$, and typically having a diameter of about 3 mm. The width of the interior of the cuvette 14 in the direction of the optical axis 12 is normally greater than 3 mm and may be about 1 cm. As a result, the illuminated region 15 may have a volume of about 70 mm$^2$.

To maximise the amount of scattered light which can be received by the detector 16, the detector is located off the optical axis 12, but as close as possible to the beam 10 without receiving any direct illumination from the beam. Further, the detector 16 is located close to the cuvette 14 to increase the amount of scattered light received by the detector. The sensitive area of the detector 16 may be about 1 mm$^2$ and it may be located at about 2 cms from the nearer wall of the cuvette 14, so that the line between the centre of the illuminated region 15 and the centre of the detector 16 forms an angle of between 5° and 7° with the optical axis 12 of the laser beam.

Figure 6:
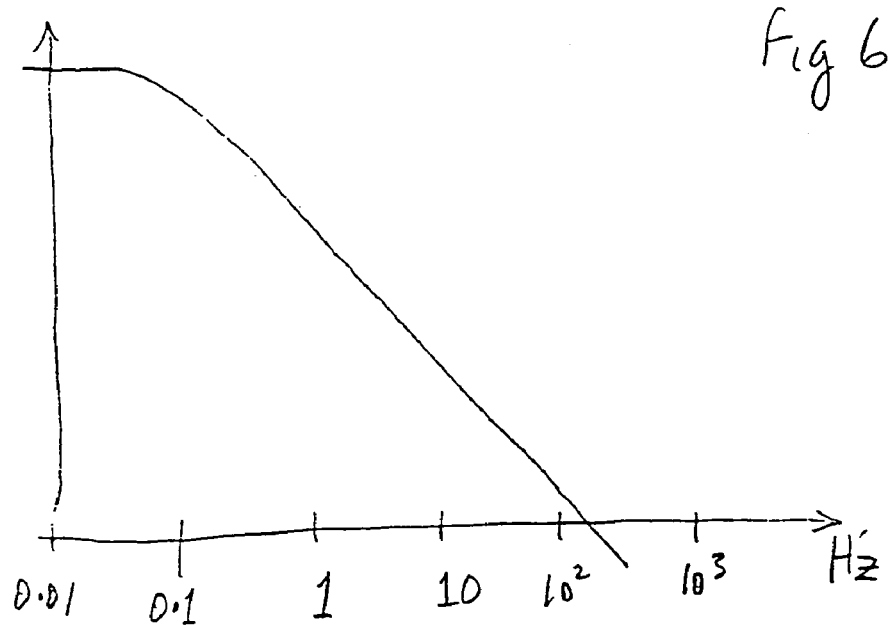
FIG. 6 is a graphical representation of a typical Lorentzian power density frequency spectrum of the fluctuations of intensity of light received at a detector which has been scattered by particles in Brownian motion in the illuminated volume of a liquid sample.

Referring now to FIG. 6, according to the theory which is known to the those skilled in this art, the power density spectrum of intensity fluctuations of the scattered light has a Lorentz distribution of the form illustrated in the Figure, on the assumption that the scattering particles are moving only with Brownian motion. For scattering particles having a size of about 1μ and a scattering angle of about 5°, the relaxation frequency or half band frequency of the spectrum is at about 0.1 Hz. It can be seen, therefore, that a very substantial part of the power in the intensity fluctuations (as much as 99%) is at frequencies below 1 Hz, and as much as 50% is below 0.1 Hz.

The embodiment of the apparatus illustrated in FIG. 1, includes a stirrer 20 illustrated adjacent a lower end of the cuvette 14, which is effective to produce a stirring motion of the liquid sample in the cuvette.

Again, the mechanism which produces the stirring action is not in itself critical. Some mechanical agitation of the liquid sample could work, although it is desirable to avoid movement of the cuvette 14 itself relative to the ion beam 10.

In a preferred embodiment, the stirrer 20 comprises a heater adapted to produce convective currents in the fluid sample.

Figure 7:
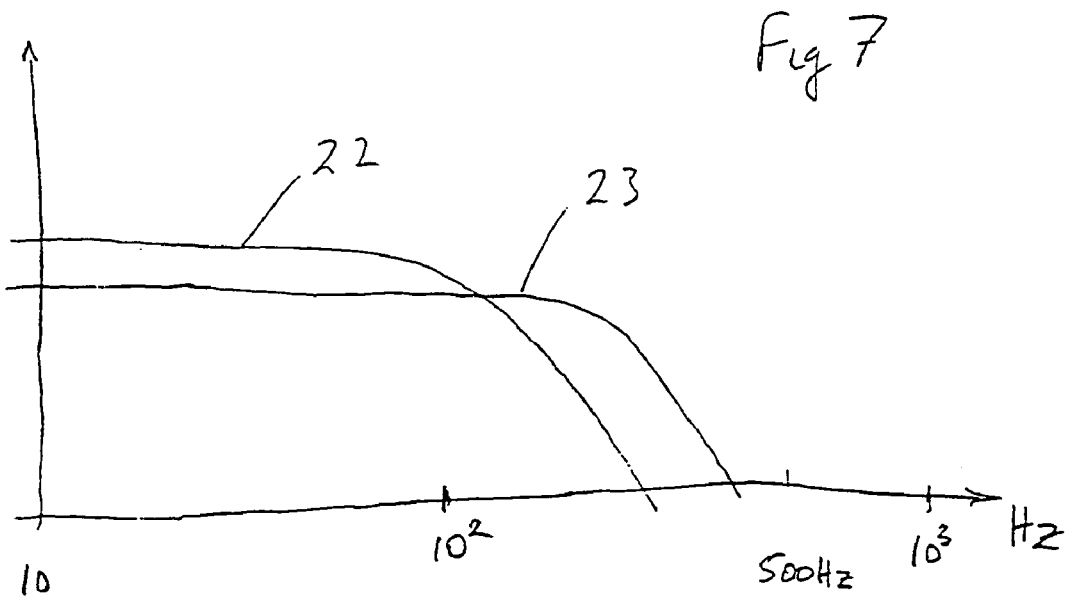
FIG. 7 is a corresponding power density distribution for particles in Brownian motion where the liquid of the sample is being stirred to produce movement of the liquid relative to the optical axis of the illuminating light beam.

The motion of the sample liquid 13 produced by the stirrer 20 has an important effect on the power density spectrum of intensity variations In the scattered-light received by the detector 16. As illustrated in FIG. 7, the movement of the sample liquid has the effect of extending the spectrum towards higher frequencies. Thus, curve 22 in FIG. 7 represents the power density spectrum from light scattered by particles in the sample liquid when the sample liquid is stirred to have a first typical speed relative to the ion beam 10 (say about 0.5 mm/s), and curve 23 represents the power density spectrum of the same sample (with the same concentration of scattering particles) but for a higher speed of movement of the sample (say about 1 mm/s). As can be seen, as the velocity of movement is increased, the relaxation frequency of the spectrum moves to higher frequency values with a simultaneous reduction in the constant power density level for frequencies below the relaxation frequency. In fact, it has been found that the relaxation frequency of the power density spectrum is substantially proportional to the velocity of movement of the liquid sample.

In the example illustrated in FIG. 7, the speed of liquid motion of about 1 millimeter per second produces a relaxation frequency of around 200 Hz.

Importantly, the increase in the relaxation frequency of the power density spectrum produced by the circulation or stirring motion of the liquid sample allows the dc filter 18 to operate with a low pass cut off of about 10 Hz. As a result, the dc filter 18 can be made to respond with a relatively shorter time constant, whilst still responding to a major portion of the total power in the intensity variation signal.

Typically, the filter 18 will also be arranged to have an upper frequency cut off to eliminate higher frequency noise and other disturbing elements from the signal. So long as the higher frequency cut off is substantially higher than the relaxation frequency, the resulting filtered signal is relatively insensitive to changes in the speed of motion of the stirred liquid sample in the cuvette 14. As can be seen from FIG. 7, the total power in the filtered signal is represented by the area under the respective curve 22 or 23 and this area does not change significantly as the relaxation frequency increases due to the compensating reduction in the constant level at lower frequencies.

Accordingly, the stirrer 20 provides an important enhancement of the sensitivity of the apparatus disclosed in FIG. 1 which also allows the filtered signal from the filter 18 to respond more quickly to changes in the concentration of scattering particles in the illuminated volume 15 of the sample.

Importantly also, the stirring effect of the liquid sample reduces any tendency for particles to settle out and ensures that the total number of particles in the illuminated volume is a fair representation of the overall concentration of particles in the whole sample 13. Also, when the apparatus is used for performing a micro biological assay, such as a growth curve analysis, the stirring effect of the sample improves response by ensuring any viable micro biological particles are continually exposed to food from the growth medium contained in the sample. This is done without the need for agitation of the cuvette 14 which could have an effect on the filtered signal from the filter 18, due to changes in intensity in the light scattered from the walls of the cuvette for example.

Figure 2:
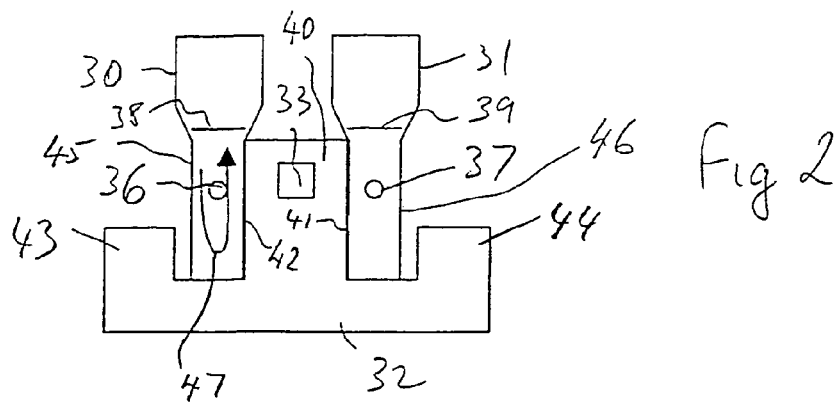
FIG. 2 is a schematic view in elevation of a pair of cuvettes containing liquid samples in a heating block for use in the apparatus of FIG. 1.

A preferred form of heater for the apparatus of FIG. 1 is illustrated in FIG. 2. In FIG. 2, two cuvettes 30 and 31 are mounted on a single heating block 32. The heating block which is also illustrated in plan view in FIG. 3, has a heating element 33 and a temperature sensor 34 providing a feedback signal to a temperature controller 35 which is designed to power the heating element 33 so as to maintain the block 32 at a predetermined temperature.

The heating block 32 is arranged to support cuvettes 30 and 31 side by side in a vertical plane which is perpendicular to the optical axes of a pair of parallel laser beams 36 and 37. Each of the laser beams 36 and 37 can be generated from a respective separate laser which is not shown in these drawings. The laser beams 36 and 37 are arranged to pass through the respective cuvettes 30 and 31 at a point below the levels 38,39 of liquid samples in the respective cuvettes, to provide illuminated regions of the respective samples in the manner as illustrated in FIG. 1.

Each of the cuvettes 30 and 31 has a rectangular horizontal cross-section. The heater block 32 is shaped substantially as a letter E with a central part 40 extending vertically between and snugly fitting against the inner facing surfaces 41 and 42 of the two cuvettes. The central part 40 extends up the height of the cuvettes to above the level of the laser beams 36 and 37 substantially to the levels 38 and 39 of the liquid samples in the cuvettes.

Outer parts 43 and 44 of the E of the heater block 32 extend vertically outside the outer faces 45 and 46 of the two cuvettes. The outer parts 43 and 44 may be spaced from the outer surfaces 45 and 46 of the cuvettes, as shown, and also do not extend to the same height as the central part 40. In fact in FIG. 2, the outer parts 43 and 44 do not extend as high as the level of the laser beams 36 and 37, but this is not critical.

Figure 3:
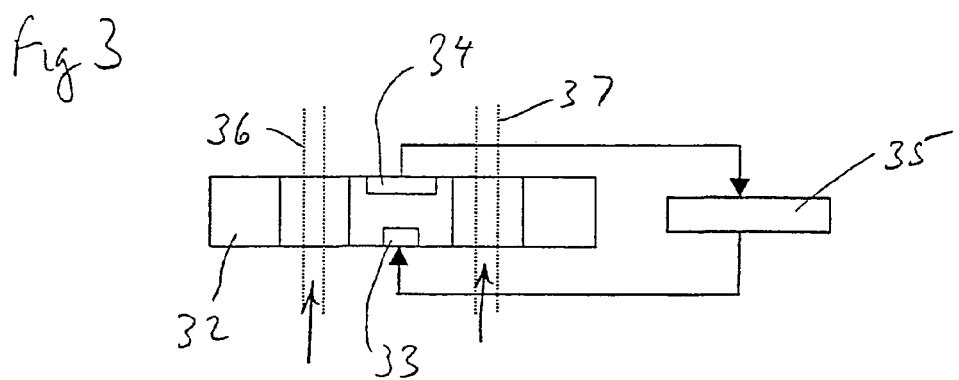
FIG. 3 is a schematic plan view of the heating block of FIG. 2 illustrating the heating and temperature control arrangement.

As illustrated in FIG. 3, the heater block 32 is substantially the same width, in the laser beam direction, as the cuvettes 30 and 31 at the plane of the laser beams, and the front and back faces of the cuvettes are exposed to receive the laser beam on one side and to allow scattered light to emerge for detection on the opposite side of the respective cuvettes.

With the asymmetric construction of the heater block 32 illustrated in FIG. 2, a sample in each of the respective cuvettes 30 and 31 is heated asymmetrically so that there will be a slight temperature difference between the inner face of the cuvette adjacent the central part 40 of the heater block, and the outer faces of the cuvettes which are generally exposed to the local ambient atmosphere. As a result, a convective current will flow in the liquid sample as illustrated by the arrow 47.

It has been found that a sufficient movement of the sample to achieve the desired objective of shifting the relaxation frequency of the power density spectrum to higher frequencies (FIG. 7) can be obtained with only a relatively small temperature difference across the sample. For example, with cuvettes 30 and 31 having a substantially square cross-section at the level of laser beams 36 and 37 of side about 1 cm, only a very small temperature difference across the liquid sample (typically about 0.1° C.) is sufficient to ensure adequate stirring motion of the liquid. Such a temperature differential can be assured with the difference between the temperature of the sample liquid within the cuvette and ambient in the vicinity of the outer faces of the cuvette, of just 3° C. This may readily be achieved when operating the heater 33 to maintain the heater block and the liquid samples in the cuvettes, substantially at a temperature of about 37° C. which is a standard temperature for promoting bacterial growth in a growth medium.

Figure 4:
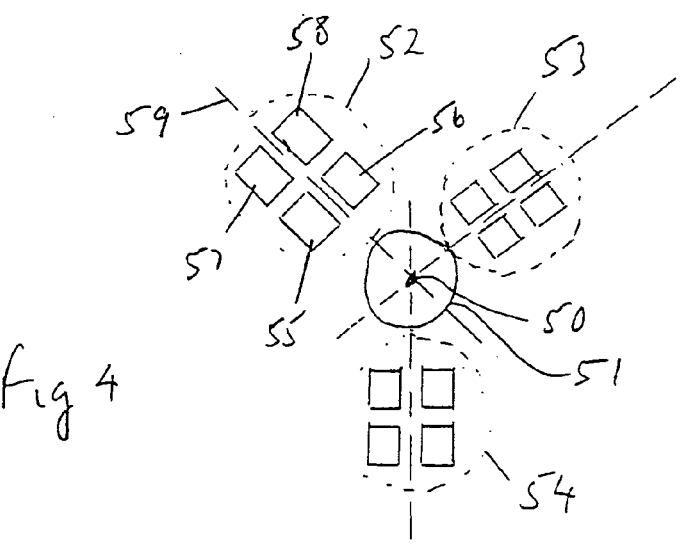
FIG. 4 is a schematic view taken along the optical axis of the laser beam illustrating an arrangement of photodetectors which may be employed in the apparatus of FIGS. 1 to 3.

Referring now to FIG. 4, this is a schematic illustration of a photodetector arrangement which may be used for detecting scattered light in embodiments of the present invention. The illustration of FIG. 4 is a view along the optical axis 50 of a laser beam 51 taken at a point substantially in the plane of the photodetectors such as photodetector 16 in FIG. 1. Instead of a single photodetector 16 as illustrated in FIG. 1, the arrangement of FIG. 4 provides twelve separate detector elements in groups of four which are mounted together in units 52, 53 and 54. Each of the units 52, 53 and 54 are similar. Considering unit 52, this contains four individual photodetector elements 56 to 58 each having sensitive surfaces about 1 mm². A preferred form of photosensitive element is the photodiode type QD7-5 from RS Components. The four photodiodes 55 to 58 are mounted in two pairs 55,56 and 57,58 with the diodes of each pair being mounted symmetrically on either side of a plane 59 containing the optical axis 50 of the laser beam 51. Thus, the two photodiodes of each symmetrical pair should receive the same dc component of intensity of scattered light. Similarly, the diodes of the pair should provide intensity variation signals having similar amplitude and frequency distribution. However, the intensity variation components of the signals will be uncorrelated with respect to each other.

In the arrangement illustrated, each of the blocks 52, 53 and 54 contain four diodes mounted together as illustrated so that there are a total of six pairs of symmetrically positioned diodes.

Figure 5:
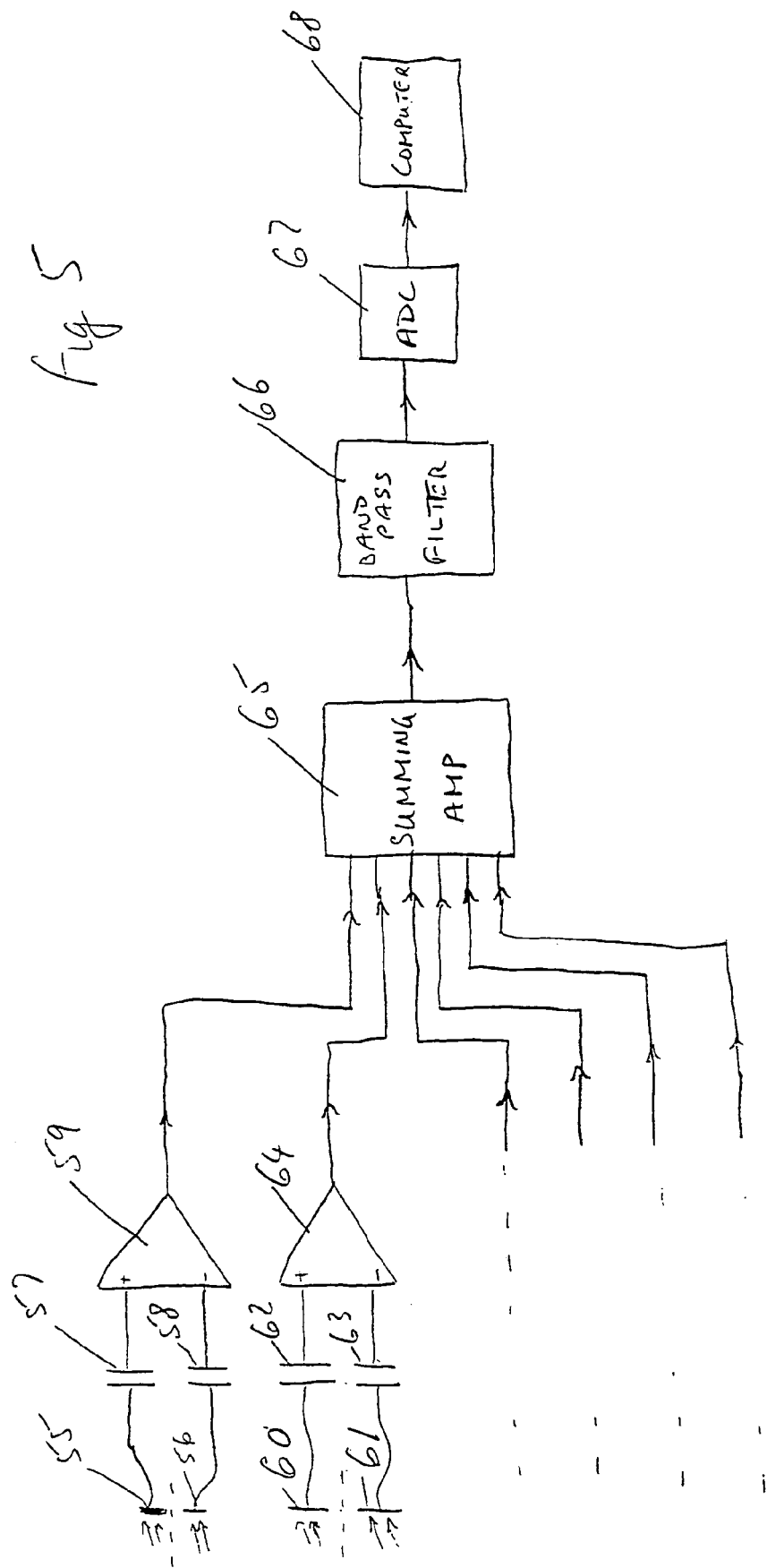
FIG. 5 is a schematic block diagram of an electronic circuit employed to provide an output signal from the apparatus.

Referring now to FIG. 5, the signals from each pair of symmetrically positioned diodes are supplied to the inverting and non inverting inputs respectively of a respective differential amplifier. Thus, the signals from photodiodes 55 and 56 are supplied via respective dc blocking capacitors 57 and 58 to a differential amplifier 59. Similarly, signals from diodes 60 and 61 are supplied via capacitors 62 and 63 to differential amplifier 64. The signals from the other pairs of diodes as illustrated in FIG. 4 are also supplied to corresponding differential amplifiers but these have been represented by dashed lines in FIG. 5 for simplicity.

The difference signals from the six differential amplifiers are then supplied to a summing amplifier 65 and the resulting sum signal is supplied to a band pass filter 66. The output of the band pass filter is A/D converted in ADC 67 and the resulting digital information provided to a computer 68.

By providing signals from symmetrically positioned and matched pairs of photodiodes to the inputs of respective differential amplifiers, any correlated varying components of the two signals from the two diodes of the pair will tend to cancel out in the output signal from the differential amplifier. Such correlated signals could for example correspond to variations in the intensity of the laser light from the laser 11. On the other hand, the intensity variations resulting from diffraction between light scattered by the different particles in the liquid sample are uncorrelated with each other so that subtracting one signal from the other in the differential amplifier 59, for example, in fact produces an intensity variation signal having an amplitude which is $\sqrt{2}$ times the amplitude of each of the intensity variations signals from the individual diodes. Accordingly, the described apparatus can significantly reduce interfering components from the intensity variation signal whilst increasing the required component.

Similarly, the output from the summing amplifier 65 will have an intensity variation amplitude which is $\sqrt{6}$ times the average amplitude of the six difference signals from the differential amplifiers, further increasing the sensitivity of the instrument.

The band pass filter 66 is arranged to pass only signals in the frequency range between about 10 Hz and about 300 Hz and the resulting signal supplied and digitised by the ADC 67 can be a sensitive and responsive measure of the concentration of scattering particles in the sample in the cuvette. The ADC 67 may comprise a standard PC sound card.

Figure 8:
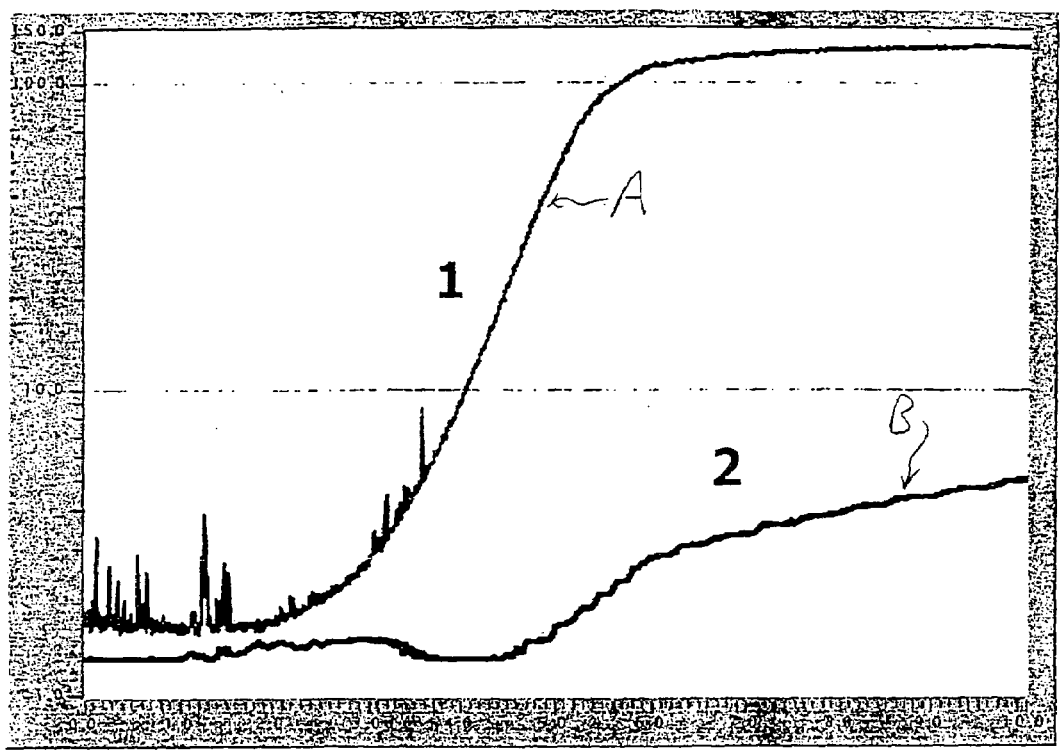
FIG. 8 is a graphical representation of a growth curve obtained by the apparatus of FIG. 1 for a sample containing a micro-organism in a growth medium.

The described apparatus can have a particular application in growth curve analysis of biological samples. Because of the high sensitivity and fast response time of the instrument, growth curves can be categorised at a relatively early stage in their development. Considering the graphical illustration of FIG. 8, this represents the growth curve of a bacterium in a sample of human urine. The background count of scattering particles in the urine sample would be typically of the order of $10^5$ parts per milliliter (ppml). Curve A indicates the development of a growth curve as measured by the above described instrument following the introduction of the sample to a growth medium. For comparison, Curve B shows the growth curve detected by a known turbidimeter for the same sample. In the illustrated example, growth of the bacteria in the sample can be detected by the above described instrument about three hours earlier even for fast growing bacteria (with a generation time of about 25 minutes). For slow growing bacteria the time improvement can be eight hours or more. This compares extremely favourably with known prior art growth curve analysis techniques.

For cleaner samples, with a lower background particle count or concentration, the development of a growth curve can be recognised even sooner.

It should be noted that advantages can be obtained in performing growth curve analysis on samples by monitoring intensity variations in the light scattered from a volume of the sample illuminated with coherent light. This can provide a more sensitive method of growth curve analysis which allows an earlier characterisation of the sample. Accordingly, although it is preferred to perform growth curve analysis with an instrument as described above in which the liquid sample is stirred in order to shift the relaxation frequency of the intensity variation power density spectrum to higher frequencies, useful results can also be obtained in the absence of any substantial stirring, although this will require a trade off between response time of the instrument and sensitivity.

A significant feature of the above described embodiment of the invention is the use of photodiodes for detection of the intensity of scattered light from the illuminated liquid sample. Prior art photometric instruments commonly use photon counting techniques for detecting scattered light, because the scattered light intensities of such prior art instruments are extremely low. This is because only a very small illuminated volume of sample is imaged to the detector, often using a large scattering angle and a narrow divergence angle, so that the detector will respond primarily to intensity variations corresponding to movement of the particles themselves. In the embodiment described above, a relatively large illuminated volume is "imaged" to the detector, so that the detector can be considered to have a sensitive area which is many times the coherence area of the speckle pattern in the detection plane. As a result of this, the output of the photodetector has a substantial dc component. However, because the amplitude of intensity variations in the detector signal are in fact also increased, filtering out the dc component of the detector signal can result in an intensity variation signal which is a sensitive measure of relatively low concentrations of scattering particles in the sample. It is important, however, that the relative magnitude between the dc component of the detector signal and the intensity variation component is not so great that the detector is either saturated by the dc component, or the intensity variation component becomes comparable to the amplitude of the noise signal produced by the detector. In the described example, the amplitude of intensity variation is typically from 0.1 to 1% of the dc component.

In the above described embodiment, a total of six pairs of symmetrically arranged photodiodes have been used to provide an enhanced intensity variation signal. Additional pairs of diodes may also be used. Furthermore arrays of large numbers of diodes could be used so long as these could be connected in pairs which are symmetrical on either side of planes containing the laser beam axis.

The invention claimed is:

1. Optical apparatus for detecting particles in a liquid medium, comprising
a container for a liquid sample with a concentration of microscopic particles in suspension;
a source of coherent light arranged to direct coherent light along a predetermined optical axis through a sample in said container to provide an illuminated volume of said sample;
a detector located off said optical axis and arranged to receive light from said source which has been scattered by particles in said illuminated volume of said sample, said detector providing a signal representing the intensity of said received light and comprising a dc component dependent on the concentration of said particles in said illuminated volume and a time varying component with frequencies in a band, a filter removing said dc component to provide a filtered output signal and a sample stirring device to produce movement of the sample liquid in said illuminated volume so as to extend said band of frequencies towards higher frequencies.

2. Apparatus as claimed in claim 1, wherein said sample storing device comprises a heater arranged to heat the sample in the container to produce convective stirring.

3. Apparatus as claimed in claim 2, wherein said heater is arranged to heat the sample differentially in a horizontal plane.

4. Apparatus as claimed in claim 3, wherein said heater comprises a heater block for receiving said container, said heater block being asymmetric about a vertical plane containing said optical axis.

5. Apparatus as claimed in claim 1, including at least a first matched pair of said detectors equally spaced at a common radial distance on opposite sides of a plane containing said optical axis, and difference means receiving input signals respectively from said pair of detectors and providing a difference signal representing the difference between said input signals.

6. Apparatus as claimed in claim 5, including at least one further said pair of detectors on opposite sides of said plane and at a respective different common radial distance from said optical axis, said difference means receiving input signals from said further pair of detectors and providing a further difference signal representing the difference between the input signals from said further pair, and a summing means receiving said difference signals and providing a sum signal representing the sum of said difference signals.

7. Apparatus as claimed in claim 5, including at least one further said pair of detectors on opposite sides of said plane and diametrically opposed to said first pair with respect to said optical axis, said difference means receiving input signals from said further pair of detectors and providing a further difference signal representing the difference between the input signals from said further pair, and a summing means receiving said difference signals and providing a sum signal representing the sum of said difference signals.

8. Apparatus as claimed in claim 5, including at least one further said pair of detectors at a common radial distance on opposite sides of a respective different plane containing said optical axis, said difference means receiving input signals from said further pair of detectors and providing a further difference signal representing the difference between the input signals from said further pair, and a summing means receiving said difference signals and providing a sum signal representing the sum of said difference signals.

9. Apparatus as claimed in claim 1, wherein the or each detector has a sensitive aperture which is greater than ten times the coherence area for interfering scattered light at the detection plane normal to the optical axis.

10. Apparatus as claimed in claim 9, wherein the illuminated volume of said sample has an area normal to the optical axis which is greater than 1 $mm^2$.

11. Apparatus as claimed in claim 9, wherein said illuminated volume has a dimension along said optical axis which is greater than 3 mm.

12. Apparatus as claimed in claim 11, wherein said dimension is greater than 7 mm.

13. Apparatus as claimed in claim 9, wherein said illuminated volume is greater than 3 $mm^3$.

14. Apparatus as claimed in claim 13, wherein said illuminated volume is greater than 30 $mm^3$.

15. Apparatus as claimed in claim 9, wherein said sensitive detector aperture is between 0.5 and 2 $mm^2$.

16. Apparatus as claimed in claim 9, wherein the distance between the mid point of the illuminated volume along the optical axis and the detection plane is between 1 and 5 cm.

* * * * *